US008636640B2

(12) United States Patent
Chang (10) Patent No.: US 8,636,640 B2
(45) Date of Patent: Jan. 28, 2014

(54) METHOD AND SYSTEM FOR BRAIN ENTERTAINMENT

(75) Inventor: Daniel Wonchul Chang, Arcadia, CA (US)

(73) Assignee: Brain Symphony LLC, Los Angeles, CA (US)

( * ) Notice: Subject to any disclaimer, the term of this patent is extended or adjusted under 35 U.S.C. 154(b) by 1155 days.

(21) Appl. No.: 12/386,006

(22) Filed: Apr. 11, 2009

(65) Prior Publication Data

US 2010/0056854 A1 Mar. 4, 2010

Related U.S. Application Data

(60) Provisional application No. 61/123,832, filed on Apr. 11, 2008, provisional application No. 61/188,421, filed on Aug. 8, 2008.

(51) Int. Cl.
*A61M 21/00* (2006.01)
(52) U.S. Cl.
USPC .......................................................... 600/28
(58) Field of Classification Search
USPC .............................. 600/26–28; 128/897–899
See application file for complete search history.

(56) References Cited

U.S. PATENT DOCUMENTS

| | | | | |
|---|---|---|---|---|
| 2,304,095 A * | 12/1942 | Hull | | 600/28 |
| 3,712,292 A * | 1/1973 | Zentmeyer, Jr. | | 600/28 |
| 5,213,562 A * | 5/1993 | Monroe | | 600/28 |
| 6,017,302 A * | 1/2000 | Loos | | 600/28 |
| 6,687,193 B2 * | 2/2004 | Jung | | 369/4 |
| 2005/0049452 A1* | 3/2005 | Lawlis et al. | | 600/28 |
| 2007/0084473 A1* | 4/2007 | Hewett | | 128/898 |
| 2008/0101621 A1* | 5/2008 | Zimmerman | | 381/61 |

OTHER PUBLICATIONS

Transparentcorp.com website dated Dec. 30, 2006, accessed on archive.org, describing Brain Sound Studio.
Pages from Brain Sound Studio product reflecting sample transforms; the Brain Sound Studio product containing these pages was on-sale in 2006.

* cited by examiner

*Primary Examiner* — Charles A Marmor, II
*Assistant Examiner* — Shannon McBride
(74) *Attorney, Agent, or Firm* — Steven E. Shapiro (57) ABSTRACT

The present invention is a method of modifying music files to induce a desired state of consciousness. First and second modulations are introduced into a music file such that, when the music file is played, both of the modulations occur simultaneously. Additional modulations can be introduced, as well as sound tones at window frequencies.

16 Claims, 4 Drawing Sheets

METHOD AND SYSTEM FOR BRAIN ENTERTAINMENT

CROSS-REFERENCE TO RELATED APPLICATIONS

The applicant hereby claims benefit of U.S. Provisional Patent Application No. 61/123,832 (filed Apr. 11, 2008). The specification of said provisional patent application is incorporated herein by this reference as though set forth in full.

The applicant hereby claims benefit of U.S. Provisional Patent Application No. 61/188,421 (filed Aug. 8, 2008). The specification of said provisional patent application is incorporated herein by this reference as though set forth in full.

STATEMENT REGARDING FEDERALLY SPONSORED RESEARCH OR DEVELOPMENT

Not Applicable.

FIELD OF INVENTION

The present invention relates to the field of brain entrainment.

BACKGROUND OF THE INVENTION

As the information technology peaks in its evolution to optimize our 'external' living conditions, the next technology or applied science to improve human conditions should focus back toward inner capacity of the human being. Optimizing human conditions in mental and physical dimensions has been sought throughout history. With all the advancement in the modern science and technology, this heavily sought goal can be realized and applicable to for a wide spectrum of the population.

The present invention includes safe and effective ways to improve brain function. The present invention uses "digitally edited" music files to entrain the listener's brain functions towards more efficient and healthier brain functions simply by listening to one's favorite music. "Brain entrainment" is to change one's brain state to a desired brain state by experiencing an entrainment method. The idea of brain entrainment has been in use throughout our history as well as our daily living. Listening to music, watching a movie, dancing, playing sports, meditation, reading, drinking coffee or alcohol, or enjoying a hobby, etc., are some examples that we use to change our brain state to "a desired state". The benefits of listening to music in improving mood, attention, and stress reduction have been well validated by numerous scientific studies.

In the present invention, special combinations of "subtly" noticeable (almost unnoticeable) sound effects on music of personal preference are introduced. The listener usually dose not notice the effects, but the brain of the listener "perceives" the special effects. subconsciously. The special sound effects carry specially arranged multiple frequencies resonating with target brain oscillating networks. The goal of the special effects is to activate the whole brain to work more harmoniously and efficiently for a target task. By experiencing (listening) the specially edited music repetitively, the listener's brain becomes more balanced, efficient and healthier as the new patterns become ingrained in one's brain (habituated, learned, formed neuroplasticity). A more balanced and healthier brain reflects a more balanced and healthier person. It is hoped that this may be a first step towards a better world and expedition of "human evolution".

The present invention incorporates its unique entrainment methods to maximize "natural" synchronous activations of the whole brain, to induce optimal brain state for a target task/activity. Other entrainment methods mostly try to maximize a dominant brain state for a target task/activity by using entrainment driven by frequency or frequencies representing the dominant brain state and the "effective" entrainment is achieved by using "strong" intensity of the entrainment frequency (clearly consciously noticeable to listener; increasing signal to ratio). One possible problem in using strong intensity is that strong intensity may coerce some oscillators into oscillating in frequencies other than their innate/natural frequencies simply by the brute force of the entrainment. This may result in an "unnatural target brain state" for the target task/activity and prevent the whole brain from working as one harmonious system. The present invention utilizes "weak intensity" (near or just below conscious recognition threshold) in the entrainment. "Weak coupling" of oscillators is one of the pre-requisite conditions for natural synchrony in complex-nonlinear oscillator systems such as in brain. To enhance sensitivity of the brain oscillators to the weak intensity-entrainment, optimal priming of brain oscillators by using personal favorite music as medium to carry the entrainment (neuro-psychological and neuro-physiological benefits of listening to music, stochastic activation of whole brain oscillators for more effective and efficient signal processing). To enhance the natural synchrony of whole brain oscillators for optimal target brain functions, auxiliary, binding frequencies as well as maximizing harmonic and golden ratio relationships among the entrainment frequencies are used. Multiple target frequencies and frequency maxima of cortex lobules are also employed to maximize effectiveness and efficacy of the entrainment for the target task/activity if applicable. "Bridging frequencies", which are frequencies located at the borders of commonly known brain wave bands (delta, theta, alpha, beta, and gamma), can also be included. Examples of the bridging frequencies are 4 Hz (delta-theta), 7.83 (theta-alpha), 12 (alpha-beta), etc. The bridging bands may render "a window" to "synchronously activate" the brain oscillators responsible for the two adjoining bands.

Accordingly, the present invention employs a very wide range of modulation frequencies. Some of the bands that can be utilized include those listed below in Table 1.

TABLE 1

| | |
|---|---|
| Slow 4 | 15-40 sec. |
| Slow 3 | 5-15 sec. |
| Slow 2 | 2-5 sec. |
| Slow 1 | 0.7 to 2 sec. |
| Delta | 0.5 to 4 Hz. |
| Theta | 4 to 8 Hz. |
| Alpha | 8 to 14 Hz. |
| Beta | 12-30 Hz. |
| Gamma | 30-80 Hz. |
| Fast | 80-200 Hz. |
| Ultra-Fast | 200-600 Hz. |

SUMMARY OF THE INVENTION

A method of modifying a music file to induce a desired brain state, comprising the following steps: Introducing a first modulation into the music file; and, introducing a second modulation into the music file such that, when the music file is played, said first modulation and said second modulation occur simultaneously. Said first modulation may comprise a main target frequency and said second modulation may comprise a secondary target frequency. The method may further comprise the step of introducing a third modulation into the music file, wherein said third modulation comprises said main target frequency and, when the music file is played, said first modulation, said second modulation and said third modulation occur simultaneously.

One or more additional modulations can be added to the above methods that comprise binding frequencies and/or auxiliary target frequencies. It is preferred that one or more harmonic relationships exist between some of the modulations. Additionally, the ratio of frequencies can be substantially the golden ratio. Further, frequencies that are substantially Fibonacci numbers (such as 89, 144, and 233) can be used. Similarly, the ratios of frequencies in brain entrainment modulation sets can be substantially golden ratios found between Fibonacci numbers, such as the ratio of 233/89 or 144/89. Modulations can comprise repeating ramping patterns. A single cycle of said ramping pattern can comprise both ramping up and ramping down. Computer storage devices that contain music files modified according to the methods described herein are also within the scope of the present invention.

It is preferred that said modulations are subtle and of weak intensity. More preferably, it is preferred that the modulations are near or just below the conscious recognition threshold.

The present invention also allows users to select their favorite songs for brain entrainment purposes. In one embodiment, typically involving a website, the user can select a music file from a music file database, select a brain entrainment modulation set from a database of brain entrainment modulation sets, and then cause the selected music file to be modified according to the selected brain entrainment modification set. The modified file can then be downloaded.

In addition, the invention can be practiced with a portable transformer. The user can download one or more brain entrainment modulation sets onto the portable transformer. The user can then connect a stand-alone music player (such an IPod or MP3 player). The portable transformer can accept the music signal from the music player, modify the song and then play the modified song through a headphone, speaker or other sound output device.

BRIEF DESCRIPTION OF THE DRAWINGS

The above and other objects and advantages of the present invention will be apparent upon consideration of the following detailed description, taken in conjunction with the accompanying drawings, in which reference characters refer to like parts throughout, and in which.

DETAILED DESCRIPTION OF THE INVENTION

I. Entrainment

Entrainment is the induction of target oscillators to resonate or respond (linear, nonlinear, chaotic, deterministic, phase change, etc) according to external stimulation carrying certain spatio-temporal information such as frequencies, special wave forms or interference patterns of waves. Brain entrainment is an example and tries to change or induce a brain state optimal for certain activity or tasks. However, entrainment can be applied to any system with its own natural frequencies such as in a biosystem across bio-molecules, cells, organs, organisms and populations. An entrainment can be applied not only to induce an optimal state of a target system, but also to correct suboptimal or pathological state of the target system.

II. Achievement of Specific Brain State

The human brain is a very complex system in its anatomical and functional interactions. A brain state in relaxation or learning, for example, is a resultant global brain function from activation of appropriately combined various 'core brain functions'. The core brain functions include arousal, attention, emotion, memory, cognition, and abstraction as well as sensory and motor systems. Each core brain function has its unique neuronal networks comprised of anatomical-functional connections of different parts of the brain. The optimal brain state for a target activity requires an appropriate proportion of activation and specific spatio-temporal communication and cooperation among the various core brain functions. The degree of activation in each core brain function varies according to a task at hand. For example, reading an article requires a proper degree of arousal, proper type of attention, proper type of emotion, activation of long and short term memory systems, activation of visual cortex and its association cortex, and proper activation of abstraction and rewarding system, etc.

The core brain functions are generated by activation of anatomical and functional brain connections among specific structures within the brain (brain stem, thalamus, limbic brain, cerebellum and cortex). These anatomical and functional connections and communication among specific parts of the brain manifest as signature oscillations in the brain. In each brain network, a brain oscillator has its "natural" frequency or frequencies, and wave form or wave forms, and communicates with other oscillators mostly by "rhythmic oscillations". The brain waves captured by electroencephalogram (EEG) or electrocorticogram (ECG) show the rhythmic oscillations and can be divided by certain frequency ranges: delta, theta, alpha, sensory-motor rhythm (SMR), beta, gamma, high gamma, etc. Each band has its unique sets of oscillator or oscillators composed of specific anatomical and functional connections among various brain structures. Each band also renders its unique brain function. A brain activity associated with a certain task requires balanced, harmonized activations and cooperation among different bands. There are also certain frequencies that are known for unique functional implications. Some examples are 6.5, 7.83, 10, 12, 13, 20 and 40 Hz.

III. Oscillators in the Human Brain

The human brain is composed of multiple anatomical and functional oscillators rendering statistically divisible several oscillatory bands covering frequencies from approximately 0.05 Hz to 500 Hz: ultra fast (200-600 Hz), fast (80-200), gamma (30-80), beta (12-30), alpha (8-12), theta (4-8), delta (0.5-4), slow 1 (0.7-2 sec), slow 2 (2-5 sec), slow 3 (5-15 sec), slow 4 (15-40 sec). Each band may represent different oscillatory classes and functions based on its unique anatomical-functional composition. Oscillations in the brain are believed to provide temporal windows that coherently bind cooperating neuronal oscillators for representation, processing, storage, and retrieval of information. Different oscillatory classes may carry different dimensions of brain integration. Appropriate coupling of different oscillator classes can provide enhanced brain functions and optimal brain state for a target brain activity. For example, slower rhythms such as alpha and theta synchronize large spatial domains and can modulate and influence faster local rhythms, such as gamma, into synchronization of local faster rhythms across widespread cortical regions that may be responsible for the 'binding' of various local functions into a coherent cognitive percept. In short, the brain uses appropriate spatio-temporal couplings (binding and synchronization) of different oscillators specific for a brain activity or a brain state. Brain oscillators belong to non-linear, limit-cycle and weakly deterministic-chaotic oscillators and share features of both harmonic and relaxation oscillators. Nonlinearity in the brain function signifies its 'surprising' sensitivity to 'weak (intensity)' external stimuli carrying specific temporal information (oscillatory frequency, specially timed pulsed waveforms, etc.), its response to a stimulus being dependent on the initial priming or state of the brain, and constructive role of 'stochastic noise' in efficiency of signal processing by stochastic resonance. Therefore, more optimal entrainment can be devised by incorporating the above-mentioned information on how the human brain functions for a particular target brain state.

IV. Present Invention

There are benefits to listening to music. For example, clinically proven benefits include improved mood, attention, memory, cognition, and autonomic function especially in the reduction of stress related physiological functions. Music effects on brain functions measured by EEG or other methods include a decrease of chaos and an increase of coherence.

Additionally, a music piece has a tremendous amount of stimulations in a wide spectrum of parameters: tonality, notes, timbre, rhythm, organization, melody, etc. Therefore, music can be a source of stochastic resonance as well as the music benefits mentioned in the above during entrainment.

Listening to one's favorite music (as opposed to music that is less enjoyable to the listener) has shown further enhancement in the benefits of music. In addition, one's favorite music may address "individual variability" of one's brain; certain music may have more optimal interactions with the unique make-up of one's brain, resulting in personal 'favor' to the music subconsciously. Favorism can also provide additional motivation to listen more often to music modified to enhance brain entrainment. In summary, favorite music can provide the optimal priming of the brain for the entrainment, induced by the benefits of music as well as stochastic resonance to oscillators of the whole brain.

In the present invention, appropriate combinations of multiple frequencies, their phase shift, and their proportional entraining 'strength' (intensity of entrainment and number of entraining methods for a frequency) over specific temporal structure-dynamic during entrainment aim to reflect an optimal brain state for a target brain activity. In other words, utilization of "cross-frequency coupling", where one frequency band modulates the activity of a different frequency band, rendering more harmonized and effective activation of the whole brain, is a core feature of the entrainment of the present invention.

Target frequencies reflect 'natural oscillatory frequencies' of neuronal network interactions mainly responsible for the target brain state. Based on a target brain state of the entrainment, there may be a primary target frequency or additional secondary target frequency, or multiple primary target frequencies, which usually are picked within or proximal to the frequency band occupying the primary target frequency. The brain functions as "a whole unit". In other words, a certain brain function or brain state such as in reading is an outcome of appropriately balanced interactions among different oscillators of whole brain. This requires "optimal" combinations of different oscillator activities for a certain brain state. Some brain oscillators have more critical functions than others for achieving a desired brain state or activity. There may be more than one oscillator playing the critical roles for the desired brain state and each oscillator has its own set of natural frequencies that it responds to. Therefore, there may be more than one target frequencies depending on the target brain state.

In addition, the present invention attempts to incorporate frequency maxima found at each brain lobule (right and left-frontal, parietal, temporal and occipital lobes) according to target brain state. For example, entrainment for a target brain state requiring major contribution from left frontal lobe function utilizes frequency maxima from the left frontal lobe.

Auxiliary frequencies reflect 'natural oscillatory frequencies' of neuronal network interactions providing optimal background brain state to maximize efficacy and effectiveness of the target brain frequencies. For example, 9 or 10 Hz from the alpha band may be used to activate thalamocortical neuronal network to recruit (synchronize) large territories of the hemispheres. Usually, slower oscillatory frequencies, alpha or theta frequencies, are used in the auxiliary frequencies. The slower frequencies provide temporal windows to include and synchronize the local faster frequencies within their oscillatory cycles.

Binding frequencies reflect 'natural oscillatory frequencies' of neuronal network interactions synchronizing local faster rhythms across widespread cortical regions, binding various local functions into a coherent global brain function. Frequencies from ultra fast (200-600 Hz), fast (80-200), or gamma (30-80) bands are used. Of special interest, I use a frequency from 36-40 Hz as a 'consciousness frequency' in addition to its role as a binding frequency.

'Harmonic relationships' among the entrainment frequencies are maximized to enhance global harmony and to amplify entrainment in the brain. An example is an entrainment with target frequencies 13 and 20, auxiliary frequencies 10, 7.83 and 4, and a binding frequency 40. These have the following harmonic relations: 4×2.5=10, 4×5=20, 4×10=40; 7.83×5=39.15 (40); 10×2=20, 10×4=40; 13×3=39 (40); 20×2=40.

'Golden ratio' relationships between entrainment frequencies are maximized when applicable. The golden ratio is defined by=(1+square root of 5) divided by 2. It is ratio of two numbers yielding 1.618033989 . . . ; it is prevalently found in 'natural' sequences or organization and geometric figures (Golden Rectangles or Golden Triangles). It may be considered as a way of mathematical illustration on how nature organizes or evolves itself. For example, the golden ratio can be found in numbers of opposite spirals in the façades of a pineapple (13/8) and a pine cone (8/5) and of the interlocking spirals in the center of a coneflower (21/13) and a daisy (34/21). Also of interest, there are special sequences of numbers occurring often in nature. The Fibonacci numbers as an example, 1, 1, 2, 3, 5, 8, 13, 21, 34, 55, 89, 144, 233, etc; the ratio between majorities of consecutive numbers approximates the Golden ratio. In the present invention, it is attempted to utilize golden ratio relationships among entrainment frequencies as long as the main scheme of the entrainment allows use of the sequential frequencies bearing the golden ratio relationships. This is an example of bio-mimicry that can be incorporated into entrainment.

Different temporal presentations of the entrainment are used: simultaneous play of all the entrainment frequencies, sequential play (for an example, auxiliary frequencies, then adding target frequencies, and then binding frequency) or other temporal combinations. Additionally, the intensities of entrainment frequencies may be constant or variable over the temporal course of entrainment bearing special codependent changes among entrainment frequencies. In general, a 180 degree phase difference of entrainment peak-intensity between lower frequencies (theta or alpha) and higher frequencies (gamma) is utilized.

Low (weak) entrainment intensity (amplitude) renders more effective entrainment than strong entrainment intensity because of brain oscillators being non-linear, limit-cycle and weakly deterministic-chaotic oscillators. The weak entrainment intensity also renders "weak" coupling with brain oscillators which may be one of required conditions for optimal synchronization among brain oscillators. In addition, strong entrainment intensity may result in "too strong" coupling which can distort any brain oscillator's amplitude significantly, coercing unnatural oscillatory frequencies and keeping brain oscillators from forming optimal synchronicity among themselves. The entrainment intensity is usually targeted at or just below threshold of 'conscious awareness' to musically untrained ears (with individual variability of the threshold), but effective in the brain entrainment. (see the following experiment data).

In one embodiment, the brain entrainment information is embedded on an individual's favorite music. The favorite music can provide an optimal priming of the individual's brain for the target brain state as well as the stochastic resonance for efficient signal processing during the brain entrainment.

The present invention enables users to control how they want to make their own entrainment music. For example, they can choose entrainment for their target brain state, then music to embed the entrainment. In addition, they can make brain entrainment music carrying a series of different songs, each embedded with different target brain state entrainment according to their needs: relaxation-concentration-creativity-relaxation, etc. The users can also be provided with the ability to select the order of songs (for example, the order of songs played on a CD). Full control of making own entrainment music by individual user can account for variability of individual brain make-ups and goals for entrainment, and enables one to make more effective entrainment music 'customized' for oneself.

For example, to better put the human brain into a mode for reading (passive learning), the following modifications can be added to a favorite piece of music:

Main Target. 13 Hz (the center of SMR, 12-15 Hz, is known for improving attention, which is good for absorbing information passively, inducing relaxed-alertness). It is preferred that one or two modulations, pulsed volume modulation with intensity of 17 out of 100, are included for this main target frequency.

Secondary Target. 20 Hz (for energizing, improving mental focus, and fighting fatigue). It is preferred that there is one modulation, cross-feed modulation with intensity of 20/100, for this frequency.

Auxiliary Targets. 10 Hz (recruiting-synchronizing-activating wide cortical territory, thereby bridging beta and theta, calming, mood elevator) and 7.83 Hz (recruiting-synchronizing-activating limbic-cortical pathways, thereby bridging alpha and theta, "Schumann Resonance", "earth's natural brain wave", improved stress tolerance, enhanced learning), alternating binaural-monoaural tone between 10 Hz and 7.83 Hz with base window frequency of 43.65 Hz and ramping intensity between 5 and 10 out of 100, 4.0 Hz (recruiting-synchronizing-activating limbic-cortical pathways, bridging theta and delta, release enkephalins-euphoria, catecholamines-memory and learning, full memory scanning and subconscious problem solving), auto-pan modulation with intensity of 25/100. It is preferred that there is one modulation for each auxiliary target frequency.

Binding Frequency. 40 Hz (synchronizing faster brain activities in different cortical territories, also 'consciousness brain frequency', harmonics of 13, 20, 10, 7.83, 4), low pass filter modulation with intensity of 15/100.

Harmonic Relations among the entrainment frequencies. 40 Hz-4, 7.83, 10, 20, 10-20, 4-20.

In the example above, the various modulations may have different intensities. For example, the main target modulations might have greater intensities than the auxiliary target or the binding frequency. Also, lower frequencies might be given greater intensities than higher frequencies. In the preferred embodiment, these modulations are all played simultaneously.

Another example, entrainment for relaxation and restoration, the following modifications can be added to a favorite piece of music.

Main Target. 0.5 Hz (for relaxation and reduction of pain). Auto-pan modulation with initial intensity of 10 out of 100 ramped up to 20 over 30 sec, then ramped down to 10 over next 30 sec, and the same ramping pattern repeats through out entrainment, is included for this main target frequency.

Secondary Target. 1 Hz (for feeling of well-being, pituitary stimulation to release growth hormone, harmony and balance). Cross-feedback modulation with initial intensity of 10 out of 100 ramped up to 20 over 30 sec, then ramped down to 10 over next 30 sec, and the same ramping pattern repeats through out entrainment, is included for this secondary target frequency (same phase as the main target entrainment).

Auxiliary Targets. 10 Hz (recruiting-synchronizing-activating wide cortical territory, bridging beta and theta, calming, mood elevator). Volume modulation with initial intensity of 20 out of 100 ramped down to 10 over 30 sec, then ramped up to 20 over next 30 sec (reverse trend of target frequencies and binding frequency), and the same ramping pattern repeats through out entrainment, is included for this main target frequency. 144 Hz binaural-monoaural tone generated by base window frequencies of 89 and 233 Hz and ramping intensity between 5 and 10 out of 100 (89, 144 and 233 are part of the Fibonacci numbers and have the Golden ratio relationships: 144/89, 233/144).

Binding Frequency. 90 Hz (synchronizing faster brain activities in different cortical territories; also for good feelings, security, well-being, balancing), Low pass filter modulation with initial intensity of 10 out of 100 ramped up to 20 over 30 sec, then ramped down to 10 over next 30 sec (same phase as the main target entrainment), and the same ramping pattern repeats through out entrainment, is included for this binding frequency.

Harmonic relations; 0.5, 1, 10, 90.

Table 2 below provides some other examples of brain entrainment modulation sets. The first column ("Target Task") lists the type of brain entrainment desired. The second column ("Main Target Freq") lists the main target frequency according the particular brain entrainment set. Similarly, the third, fourth and fifth columns identify the secondary target frequencies, the auxiliary frequencies and the binding frequencies (if any) of the particular brain entrainment sets. The sixth column ("Harmonic Relations") identifies any harmonic relationships that exist between the frequencies of the various modulations. Finally, the seventh column identifies Golden Ratio relationships that exist among the modulations of the particular brain entrainment set.

TABLE 2

| Target Task | Main Target Freq | Secondary Target Freq | Auxillary Freq | Binding Freq | Harmonic Relations | Golden Ratio |
|---|---|---|---|---|---|---|
| Active learning | 6 (theta) | 3.5 (delta-theta), 14 (SMR) | 9, 12 (alpha), 89, 144, 233 (fast) | 32 (gamma) | 6-12-32, 3.5-14 | 144/89, 233/144 |
| Active learning | 6 (theta) | 3.5 (delta-theta) | 10.6 (alpha), 89, 144, 233 (fast) | 32 (gamma) | 10.6-32 | 144/89, 233/144 |
| Active learning | 7.5 (theta) | 3.5 (delta-theta) | 10.6 (alpha), 89, 144, 233 (fast) | 32 (gamma) |  | 144/89, 233/144 |
| Active learning | 7.5 (theta) | 14 (SMR) | 10.6 (alpha), 89, 144, 233 (fast) | 32 (gamma) |  | 144/89, 233/144 |
| Creativity | 3.5 (delta-theta) | 7.5 (theta) | 12 (alpha), 89, 144, 233 (fast) | 32 (gamma) | 12-144 | 144/89, 233/144 |
| Passive learning | 12 (alpha) | 20 (beta) | 10 (alpha), 89, 144, 233 (fast) | 40 (gamma) | 10-20-40, 12-144 | 144/89, 233/144 |
| Passive learning | 14 (SMR) | 20 (beta) | 10.6 (alpha), 89, 144, 233 (fast) | 32 (gamma) |  | 144/89, 233/144 |
| Feeling of well-being | 1 (delta) | 3.5 (delta-theta), 10 (alpha), 90 (fast) | 89, 144, 233 (fast) |  | 1-10-90 | 144/89, 233/144 |
| Feeling of well-being | 1 (delta) | 3.5 (delta-theta), 12 (alpha), 90 (fast) | 89, 144, 233 (fast) |  | 12-144 | 144/89, 233/144 |
| Feeling of well-being | 1 (delta) | 3.5 (delta-theta), 10 (alpha), 90 (fast) | 89, 144, 233 (fast) | 38 (gamma) | 10-90 | 144/89, 233/144 |
| Feeling of well-being | 7.83 (theta) | 3.5 (delta-theta), 10 (alpha), 90 (fast) | 89, 144, 233 (fast) |  | 10-90 | 144/89, 233/144 |
| Feeling of well-being | 3.5 (delta-theta) | 1.45 (delta), 12 (alpha) | 89, 144, 233 (fast) | 33 (gamma) | 12-144 | 144/89, 233/144 |
| Good mood | 1 (delta) | 1.45 (delta), 10 (alpha) | 10 (alpha), 89, 144, 233 (fast) | 38 (gamma) | 1-10, 1-38 | 144/89, 233/144 |
| Good mood | 1.45 (delta) | 1 (delta), 12 (alpha) | 12 (alpha), 89, 144, 233 (fast) | 90 (fast) | 1-12, 1-90 | 144/89, 233/144 |
| Peak performance | 14 (SMR) | 20 (beta) | 12 (alpha), 89, 144, 233 (fast) | 32 (gamma) | 12-144 | 144/89, 233/144 |
| Peak performance | 14 (SMR) | 20 (beta) | 10.6 (alpha), 89, 144, 233 (fast) | 32 (gamma) |  | 144/89, 233/144 |
| Peak performance | 14 (SMR) | 20 (beta) | 9 (alpha), 89, 144, 233 (fast) | 32 (gamma) |  | 144/89, 233/144 |
| Relaxation-restoration | 1 (delta) | 0.5 (delta), 90 | 10 (alpha), 89, 144, 233 (fast) |  | 0.5-1-10-90 | 144/89, 233/144 |
| Relaxation-restoration | 1.45 (delta) | 4 (theta) | 10.5 (alpha), 89, 144, 233 (fast) | 38 (gamma) | 4-144 | 144/89, 233/144 |
| Relaxation-restoration | 7.83 (theta) | 10 (alpha), 90 (fast) | 89, 144, 233 (fast) |  | 10-90 | 144/89, 233/144 |
| Relaxation-restoration | 10 (alpha) | 12 (alpha) | 90 (fast), 89, 144, 233 | 36 (gamma) | 10-90, 12-36-144 | 144/89, 233/144 |

It should be noted that in Table 2 above, "SMR" stands for "sensory-motor strip rhythm", which is usually defined at 13-15 Hz. SMR appears to provide calm and/or focus. It should also be noted that not all brain entrainment modulation sets comprise binding frequencies. Binding frequencies are usually used in activities using cognition or activating consciousness, so in relaxation or calming situations, binding frequencies are not always included.

As a general rule; there can be extraordinary sensitivity of nonlinear-brain oscillators to weak signal with proper temporal information and stochastic noise. Accordingly, it is preferred that the present invention uses weak intensities for modulations. "Weak intensity" means a small quantity of stimulatory power, which may be effective and efficient to 'selectively' entrain its target brain oscillators (whose natural frequencies have matching physiological-correspondences to the entraining frequencies), and its effective-efficient quantity depends on the initial priming of the oscillators, presence of stochastic resonance and appropriate target temporal information (frequencies, phase, wave form, etc) embedded in the stimulation.

It should be noted that brain oscillators not only resonate with low frequency modulation, but also with a note carried by a tone (window frequency). There are some specific window frequencies that are associated with certain brain functions. For example, a lower window frequencied tone such as 62 Hz may enhance physical energy, 333 Hz may enhance inspiration, or 349 Hz may enhance the feeling of love, etc. In addition to and in combination with the modulations described above, one or more selected window frequencied tones can be used in generating binaural, monoaural or isochronic beats, so as to provide the optimal entrainment for an entrainment target. Generally, specific window frequency or frequencies are selected from the range of 50 to 1000 Hz.

V. Types of Entrainment Techniques

Various techniques can be used to add modulations to the music. These techniques might be applied to a wave file, for example, to create a second wave file that contains the modulations. Some of these digital editing techniques include pulse (music volume modulation at a certain frequency), binaural (simultaneous play of two musical tones with different frequencies to the right and left ear, resulting perception of the frequency which is the frequency difference of two tones), cross-feed modulation (feeding stereo sound between the right and left sides at certain frequency), low-pass filter modulation (removes high frequencies of the music file at a certain frequency), auto-pan modulation (increases or decreases the volume of the left and right sides at certain frequency). Other known editing techniques can also be used, such as reverberation of right and left channels, reverberation of front and rear channels, and monoaural tone.

It should be noted that the present invention can used with other means of stimulation other than sound (e.g., ultrasound, EMW (radio, microwave, light, magnetic, etc), mechanical vibration). The present invention may also utilize principle of wavelet, Fourier's transformation, hologram, etc.

VI. Experimental Data

Correlations between EEG measures and intelligence have been reported in numerous studies. Increased EEG power in the alpha and the beta band has been positively related with high intelligence. The network measures of EEG (coherence, amplitude asymmetry and phase delay) typically report a positive correlation of intelligence to faster processing in frontal connections (shorter phase delay of frontal connections) and widespread neural complexity-differentiation (low coherence in the widespread brain, and high amplitude asymmetry and long phase delay in the parietal and occipital-brain). Lastly, optimal levels of arousal (high EEG power in the alpha and beta band and low EEG power in the delta band) may also play a significant role in high intelligence.

The following sample EEG data were obtained from a healthy 28 year old subject after listening to brain entrainment music developed with the present invention. The music file used in the experiment included simultaneous playing of the following entrainment frequencies: primary target 13, secondary target 20, auxiliary 4-7.83-10, and binding 40. EEG was recorded before and after listening to the music with entrainment. The EEG was transformed into the time averaged power spectrum by the fast Fourier transformation (FFT), and the absolute power, the amplitude asymmetry, the coherence and the phase lag (delay) were calculated for the pre-music and the post-music EEG records. Then, differences between the pre-music and the post-music EEG measures were calculated and the summaries were tabulated below.

TABLE 3

EEG power changes in different frequency bands
(postmusic power − premusic power)
FFT Absolute Power Difference (uV Sq)

|  | Delta 1.0-4.0 Hz | Theta 4.0-8.0 Hz | Alpha 8.0-12.0 Hz | Beta 12.0-25.0 Hz |
| --- | --- | --- | --- | --- |
| Frontal | −2.06817 | 0.035514 | 0.507986 | 1.349327 |
| Parietal | 0.238238 | 0.237919 | 0.988855 | 2.37972 |
| Occipital | −0.25531 | 0.378248 | 4.098792 | 3.957911 |
| Temporal | −0.26666 | 0.118243 | 1.00812 | 1.004623 |
| Midline | −0.28923 | 0.288964 | 1.120391 | 2.121257 |
| AVG | −0.52822 | 0.211778 | 1.544829 | 2.162567 |

Positive values indicate increase of the EEG power after listening to the music and negative indicating decrease of the EEG power. There is significant increase of the alpha and beta band EEG power which has positive correlation to higher intelligence. Reduction of the delta EEG power as well as higher alpha and beta power may indicate improved arousal.

TABLE 4

The amplitude asymmetry changes in different frequency bands
(post-music amplitude asymmetry − pre-music amplitude asymmetry)
FFT Amplitude Asymmetry Difference

|  | Delta 1.0-4.0 Hz | Theta 4.0-8.0 Hz | Alpha 8.0-12.0 Hz | Beta 12.0-25.0 Hz |
| --- | --- | --- | --- | --- |
| Frontal Pole | −25.8515 | −9.26157 | −6.62464 | −6.95288 |
| Frontal | −4.52104 | 2.232517 | −5.7564 | 0.212741 |
| Central | 15.13005 | 2.409128 | 2.786828 | 7.301531 |
| Parietal | 17.12817 | 3.930166 | 10.76838 | 9.17982 |
| Occipital | −2.39672 | 3.141814 | 14.02479 | −2.7017 |
| Temporal | −5.17159 | −5.92475 | −11.325 | −9.89949 |

Positive values indicate lager amplitude asymmetry after listening to the music and negative indicating smaller amplitude asymmetry. There are predominant changes towards larger amplitude asymmetries in the parietal and occipital areas which has positive correlation to higher intelligence.

TABLE 5

The coherence changes in different frequency bands (postmusic coherence-premusic coherence)

|  | Delta 1.0-4.0 Hz | Theta 4.0-8.0 Hz | Alpha 8.0-12.0 Hz | Beta 1 12.0-15.0 Hz | Beta 2 15.0-18.0 Hz | Beta 3 18.0-25.0 Hz | High Beta 25.0-30.0 Hz |
|---|---|---|---|---|---|---|---|
| Frontal Pole | 1.201566 | 1.73888 | 12.19602 | 2.064968 | 3.130233 | −1.35306 | −3.72074 |
| Frontal | 0.600826 | 0.148135 | 9.320278 | 1.415749 | 1.163403 | −1.53292 | −1.13953 |
| Central | 0.184601 | −1.06582 | 6.678412 | 0.546687 | −0.11074 | −2.05146 | 0.112445 |
| Parietal | −0.39807 | −1.36489 | 6.37795 | 1.485628 | −0.59629 | −3.8468 | 1.229652 |
| Occipital | 0.089541 | −0.73833 | 5.69216 | 1.556764 | −1.67304 | −2.23053 | 2.441093 |
| Temporal | 1.513216 | 0.715221 | 9.77164 | 3.616797 | 1.147255 | −1.49731 | −0.2353 |
| Midline | 4.623566 | −2.72942 | 4.985236 | −2.96003 | 1.9035 | −6.2998 | −2.93906 |

Positive values indicate higher coherence after listening to the music and negative indicating lower coherence. There are lower beta2 and beta3 coherences in the parietal and occipital areas which has positive correlation to higher intelligence. There are also higher coherences across the alpha and beta1 bands suggesting increased influence of the thalamocortical oscillations providing temporal window for synchronization of faster local activities.

TABLE 6

The phase lag changes in different frequency bands (post-music phase lag − pre-music phase lag) FFT Phase Lag Difference (Deg)

|  | Delta 1.0-4.0 Hz | Theta 4.0-8.0 Hz | Alpha 8.0-12.0 Hz | Beta 12.0-25.0 Hz |
|---|---|---|---|---|
| Frontal Pole | 9.039807 | −10.0606 | −13.5808 | −6.62536 |
| Frontal | 4.833648 | −0.75654 | −8.90163 | −3.10543 |
| Central | 2.108318 | −1.22315 | −4.30908 | −1.47164 |
| Parietal | −3.52584 | −0.07179 | 0.981638 | 0.316739 |
| Occipital | −11.6815 | 11.56418 | 9.645469 | 2.721287 |
| Temporal | 3.10981 | −3.78096 | −4.91546 | −0.41377 |

Positive values indicate longer phase lag after listening to the music and negative indicating shorter phase lag. There are predominant changes towards shorter alpha and beta phase lag in the frontal area and towards longer alpha and beta phase lag in the parietal and occipital areas which has strongest positive correlation to higher intelligence.

VII. Implementation

Methods of and technology for modulating sound is well known in the art. Such methods and technologies can be utilized to create the modulations used in the present invention. Some such technologies and methods are described in U.S. Pat. No. 5,356,368, U.S. Pat. No. 6,135,944, and US Published Patent Application 2007/0084473. Each of these published documents is incorporated herein as though set forth in full.

In the context of the present invention, two basic approaches are preferred. First, a digital file can be modified to contain the desired modulations. Second, a sound file can be modulated in real-time while in use.

With respect to modifying a digital sound file, software is currently available for modulating sound files. Such commercially-available software can be used to apply the digital modulation techniques described above. For example, a digital wave file can be modified into a new wave file containing the desired modulations. One currently available software is Brain Sound Studio, which is marketed by the Transparent Corporation of Columbus, Ohio.

With respect to modulating a sound file in real-time, electronics can be utilized with a standard music-playing device (such as an IPod) to overlay the desired modulations. A low-frequency oscillator (or "LFO") can be used for this purpose. LFO's are commonly used in the music industry to modulate electronic music. An LFO is a secondary oscillator that operates at a significantly lower frequency, typically around or below the threshold of human hearing (which is approximately 20 Hz). This lower frequency or control signal is used to modulate the audio signal, changing it without introducing another sound-signal source. Like a standard oscillator, this usually takes the form of a periodic waveform, such as a sine, sawtooth, triangle or square wave. Also like a standard oscillator, LFOs can incorporate any number of waveform types, including user-defined wavetables, rectified waves and random signals. Using a low-frequency oscillation signal as a means of modulating another signal introduces complexities into the resulting sound, such that a variety of effects can be achieved. For purposes of the present invention, a LFO can be introduced between the music-playing device and an auditory device (speaker, headphones). The LFO can be programmed to modulate the music signals to achieve the desired brain entrainment, as described above. The LFO might, for example, might plug into the earphone jack (line out) of an IPod for this purpose.

For purposes of the present invention, a multiple number of LFO's can be used to modify a sound signal. This allows several modulations to be combined into one sound signal. In addition to a LFO (or instead of), a notch filter, band pass filter, or pulse modulator might be used to introduce entrainment frequencies into a sound signal. Many different combinations of these devices are possible.

Figure 4:
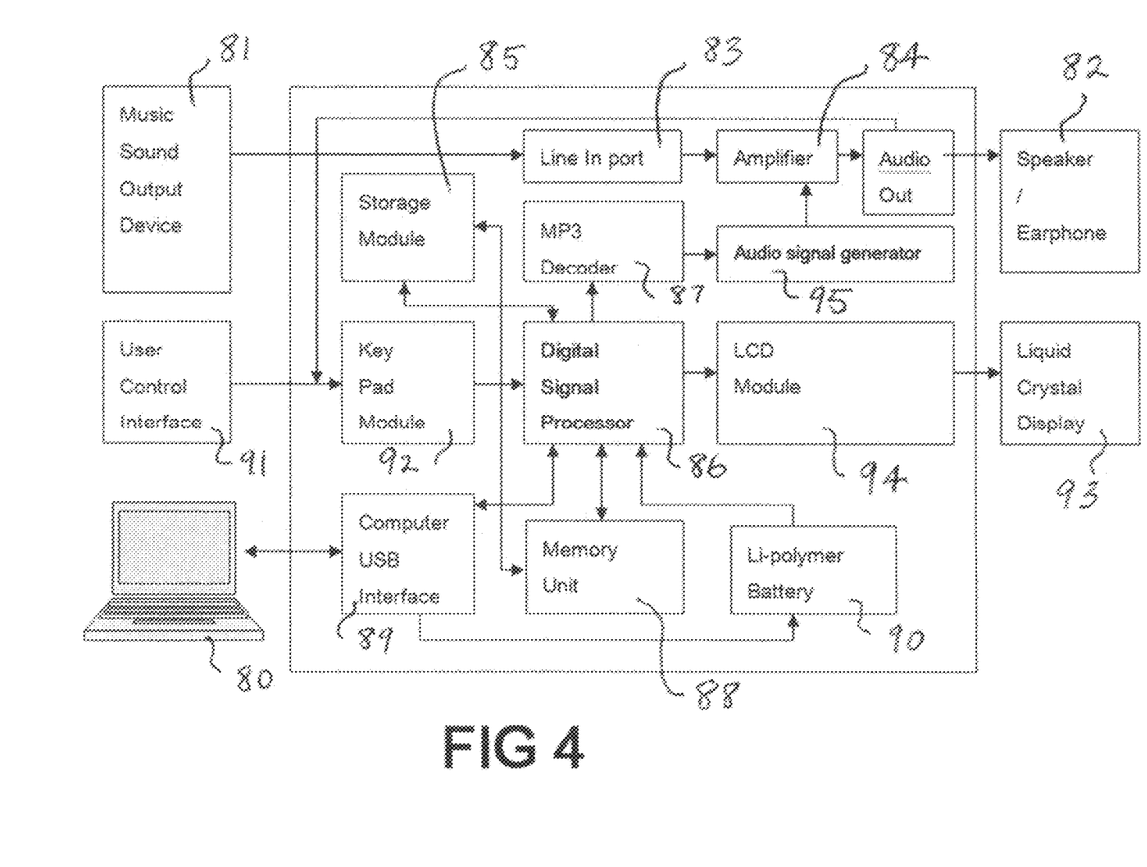
FIG. 4 shows the architecture of a portable transformer.

FIG. 4 shows the architecture of a portable transformer. The user, with a personal computer 80, can input a brain entrainment modulation set (perhaps from the Internet). The user can also connect his or her personal music device 81, such as an IPod or MP3 player. The portable transformer combines a song with a brain entrainment modulation set and outputs it through a speaker or microphone 82.

As can be further seen in FIG. 4, the music sound output device 81 inputs music via a line in port 83. The signal in turn is amplified by an amplifier 84. A storage device 85 stores available brain entrainment modulations sets. A set can be downloaded from the storage module to a digital signal processor 86 (operatively connected to a memory unit 88), and then input into a MP3 decoder 87 to be overlaid over the sound via an audio signal generator 95.

In the preferred embodiment, the computer 80 can communicate with the device via a USB interface 89. The USB interface can be used to charge the battery 90, which powers the device. The device can also be controlled through a user control interface 91 and key pad module 92. In the preferred embodiment, the portable transformer has an liquid crystal display 93 operatively connected to an LCD module 94.

VIII. Marketing

There are many different ways in which the invention can made available to consumers. One way is to make digital music files created according to the present invention available to consumers via the Internet. For example, Itunes makes digital music files available to consumers for a current cost of $0.99 per file. A company like Itunes could also make those same files available to consumers, but with the files modified according to the present invention. For example, a consumer might have a selection of a particular item of music unchanged, as well as several other files with the same song but modified to entrain the brain in specific ways. It would be possible to charge an additional sum for each song purchased that has been modified according to the invention. It would be possible for the Internet system to store just unmodified files but modify the music files when modifications are selected by consumers. For example, the user might select a favorite song and request that the song be modified to help the user relax. The system could then modify the song file and provide the modified file to the user.

1. Glossary of Internet Terms

In the preferred embodiment, the present invention utilizes a computer network, such as the Internet, as a means to provide users with the ability to select music and modify the music for brain entrainment purposes. In the preferred embodiment, the present invention comprises a web site. It can also operate by virtue of an intranet, extranet or other computer network environment. The following glossary of terms, although well known to those skilled in the applicable art, is useful with respect to understanding and comprehending the nature of the preferred embodiment:

Browser: A program used to view, download, upload, surf or otherwise access documents (pages) on the World Wide Web.

Button: A graphic that a user can "click on" to do something, such as download a program or go to another Web page.

Client: A machine that provides commands to a server, and is serviced by the server.

Cookie: A message given to a Web browser by a Web server. The browser stores the message in a text file. The message is then sent back to the server each time the browser requests a page from the server.

Extranet: The connecting of two or more intranets.

Database: A file composed of records, each containing fields together with a set of operations for searching, sorting, recombining, and other functions.

Database Engine: The program module or modules that provide access to a database management system (DBMS).

Database Management System: A software interface between the database and the user. A database management system handles user requests for database actions and allows for control of security and data integrity requirements.

Database Server: A network node, or station, dedicated to storing and providing access to a shared database.

Document: When used in reference to the World Wide Web, a document is any file containing text, media or hyperlinks that can be transferred from a server to a client program.

Electronic Mail or E-mail: Messages automatically passed from one computer user to another, often through computer networks and/or via modems over telephone lines.

File: A collection of data or information that has a name, generally called the "filename." Almost all information stored in a computer must be in a file. There are many different types of files: data files, text files, program files, directory files, and so on. Different types of files store different types of information. For example, program files store programs, whereas text files store text.

Home Page: A multi-media table of contents that guides a Web user to stored information on the Internet. A web site has a home page generally available to the public over the WWW.

HyperText Markup Language (HTML): HTML is the language commonly used by Web servers to create and connect documents that are viewed by Web clients. HTML uses Hypertext documents. The preferred embodiment of the present invention includes a web site containing documents created and connected by HTML or XML (described below).

Intranet: A private network inside a company or organization that uses the same kinds of software that you would find on the public Internet, but that is only for internal use. As the Internet has become more popular many of the tools used on the Internet are being used in private networks, for example, many companies have Web servers that are available only to employees. Note that an "Intranet" may not actually be an Internet, it may simply be a network.

Internet ("the Net"): A connection system that links computers worldwide in a network.

IP: A unique number that identifies a particular computer in a network of computers.

Link: Text and/or an image area on a Web page that a user can click on to "connect to" or reference another document. There are many possibilities of what that document can be. Most commonly links are thought of as what connects two Web pages or Web sites. They can also however be referencing a different part of the same document, linking to a file which will download to the user's computer or triggering the launching of an external or helper application which will then process the clicked on file.

Mailbox: The directory on a host computer where e-mail messages are stored.

Menu: A list from which the user may select an operation to be performed. This is often done with a mouse or other pointing device under a graphical user interface but may also be controlled from the keyboard.

Mouse: The most commonly used computer pointing device, first introduced in 1968. The mouse is a device used to manipulate an on-screen pointer that is generally shaped like an arrow. With the mouse in hand, the computer user can select, move, and change items on the screen.

Password: A secret combination of letters and other symbols needed to login to a computer system.

Server: A machine (computer) that performs a task at the command of another machine ("client"). In the context of the present invention, a server's primary function is to facilitate distribution of information over the Web.

URL: Universal Resource Locator, a Web document version of an e-mail address, in character string form, that uniquely identifies a document, application, or tool available over the Web. The description of the preferred embodiments describes a web site with multiple pages, including a home page. These are all accessible via an appropriate URL.

Web Browser: A program running on a user-operated client computer.

Web Page: <World-Wide Web> A block of data available on the World-Wide Web, identified by a URL. In the simplest, most common case, a web page is a file written in HTML, stored on the server. It may refer to images which appear as part of the page when it is displayed by a web browser. It is also possible for the server to generate pages dynamically in response to a request, e.g. using a CGI script.

Web Site: A home and/or location on the World Wide Web. A place made up of web pages. These pages can contain graphics, text, audio, video and other dynamic and/or static materials.

Welcome Page: The introductory web page for a web site, also referred to as the home page. The first page of a web site to contain some welcome and/or navigation information about the Web site.

World Wide Web (WWW or "the Web"): The Internet's application that lets people seeking information on the Internet switch from server to server and database to database by clicking on highlighted words, icons, images or phrases of interest. An Internet Web server supports clients and provides information.

XML or eXtensible Markup Language: A programming language/specification developed by the W3C. XML is a pared-down version of SGML, designed especially for Web documents. It enables Web authors and designers to create their own customized tags to provide functionality not available with HTML.

2. Basic System Architecture

In the preferred embodiment, the web site comprises a relational database management system interlinking a series of databases residing on one or more database server. Those databases can include, for example, the following:

a. Consumer Database—includes data relating to consumers that are members of the web site and who are authorized to have access to the system. In the preferred embodiment, each consumer is given a unique ID number for the database. The database includes identifying information (name, etc.), demographic information (age, etc.), and financial information (credit card information, monetary deposit information, etc.).

b. Searchable Music File Database—includes music files in one or more standard (e.g., WAV or MP3) and/or proprietary formats. This database is searchable by consumers. Consumers might be able to search, for example, based on artist (e.g., "Coltrane" or "Beatles"), title (e.g., "Born to Run", "Stairway" or "Dock"), and musical genre (e.g., "Rock", "Jazz" or "Classical").

c. Searchable Brain Entrainment Modulation Sets Database—includes brain entrainment modulation sets (these also can be in music formats such as WAV or MP3). In the preferred embodiment, each brain entrainment modulation set has a title (e.g., "Creativity", "Relaxation and Restoration", or "Good Mood").

In the preferred embodiment, the various databases are maintained on a website. A consumer can access the website, in part, utilizing a browser on personal computer or client. The website will generally be accessed via the Internet although it is possible to practice the invention through other means, such as an Extranet or an Intranet.

Initially, the consumer will be provided access to a home page for the website. The homepage will generally be in HTML, XML, or both. In the preferred embodiment, the homepage will present a menu that allows the consumer to either log in (if he or she already has an account) or to set up an account (if the consumer is a new user). If the consumer is already a member of the website, he or she can log in using a password (FIG. 1, item 1).

After the consumer has logged in, the user is sent to a welcome page, whereby the user is presented with various buttons. For example, buttons may permit the user to search the Music File Database according to desired criteria utilizing a database engine to access the database management system (FIG. 1, item 2). The web page might also allow the user to type in selection criteria, such as part of a song title or the last name of a particular artist. Other buttons might, for example, link the consumer to his or her account information.

In the preferred embodiment, after the user performs a search, the user is presented with a list of music files that match the search criteria. The list might include just one music file or thousands of such files. The user then selects a desired music file, perhaps by using a mouse (FIG. 1, item 3).

Figure 1:
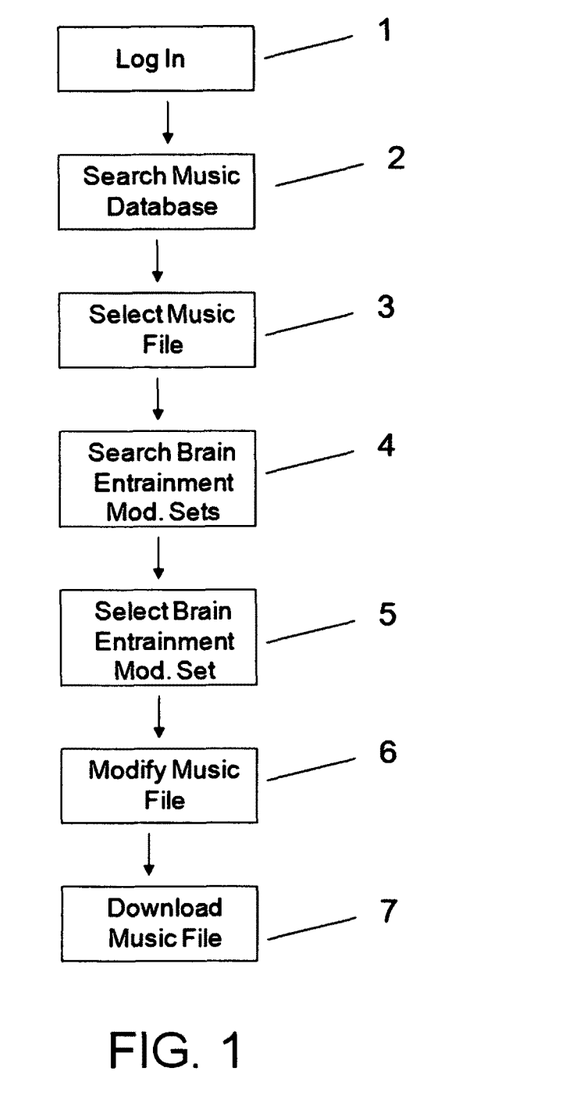
FIG. 1 provides a flow chart that shows one method by which a user can choose a favorite song, modify the song according to a selected brain entrainment modification set and download the modified song.

After selecting a music file, the user can then search or view brain entrainment modulation sets (FIG. 1, item 4). The user can then select the desired brain entrainment modulation set (FIG. 5, item 5). The user then selects a button to modify the selected music file according to the selected brain entrainment modification set (FIG. 1, item 6).

After the selected music file has been modified, the user can then download the file (FIG. 1, item 7). In the preferred embodiment, the consumer can download the modified music file directly to his computer or other device (e.g., MP3 player) or have it e-mailed to himself or elsewhere (e.g., to a friend as a gift). It is also possible to modify a plurality of music files and then download them at once. Additionally, the order of the operation shown here can be changed. For example, the user might be able to first select a plurality of music files and then modify each of them at once according to a single selected brain entrainment modification set.

3. Structure and Design of Apparatus

Figure 2:
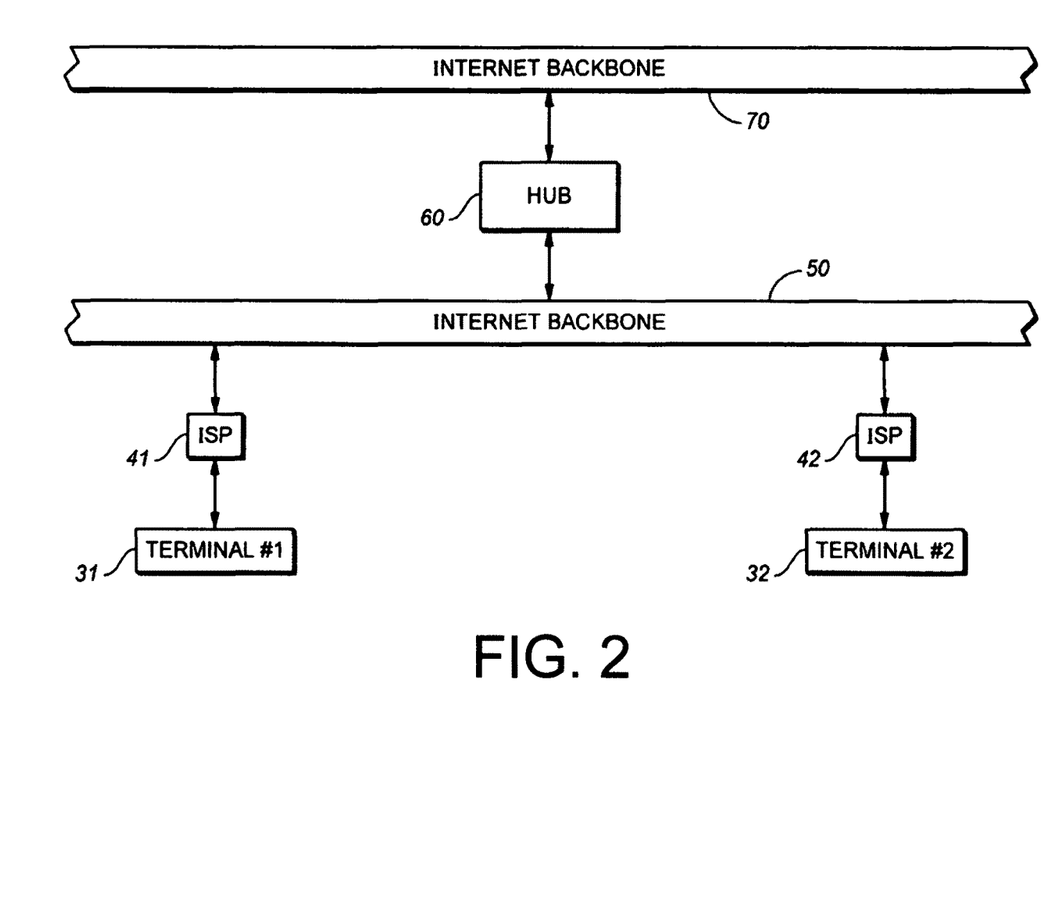
FIG. 2 is a block diagram of an environment in which the present invention can be practiced.

FIG. 2 is a block diagram illustrating the structure of the preferred network in which the present invention operates. Shown in FIG. 2 are terminals 31 and 32, each of which may comprise an ordinary computer workstation, a laptop computer, or special-purpose computing equipment. Terminals 31 and 32 communicate with Internet service providers (ISPs) 41 and 42 via a telephone connection, such as by using a modem interface. ISPs 41 and 42, in turn, connect to Internet backbone 50 via their respective routers (not shown). Specifically, ISP 41 receives Internet messages from terminal 31 and then routes them onto Internet backbone 50. Also, ISP 41 pulls messages off Internet backbone 50 that are addressed to terminal 31 and communicates those messages to terminal 31 via the telephone connection. In a similar manner, terminal 32 also can communicate over the Internet through ISP 42. Of course, such terminals may also connect directly to Internet backbone 50 if provided with the appropriate routers and other hardware.

Figure 3:
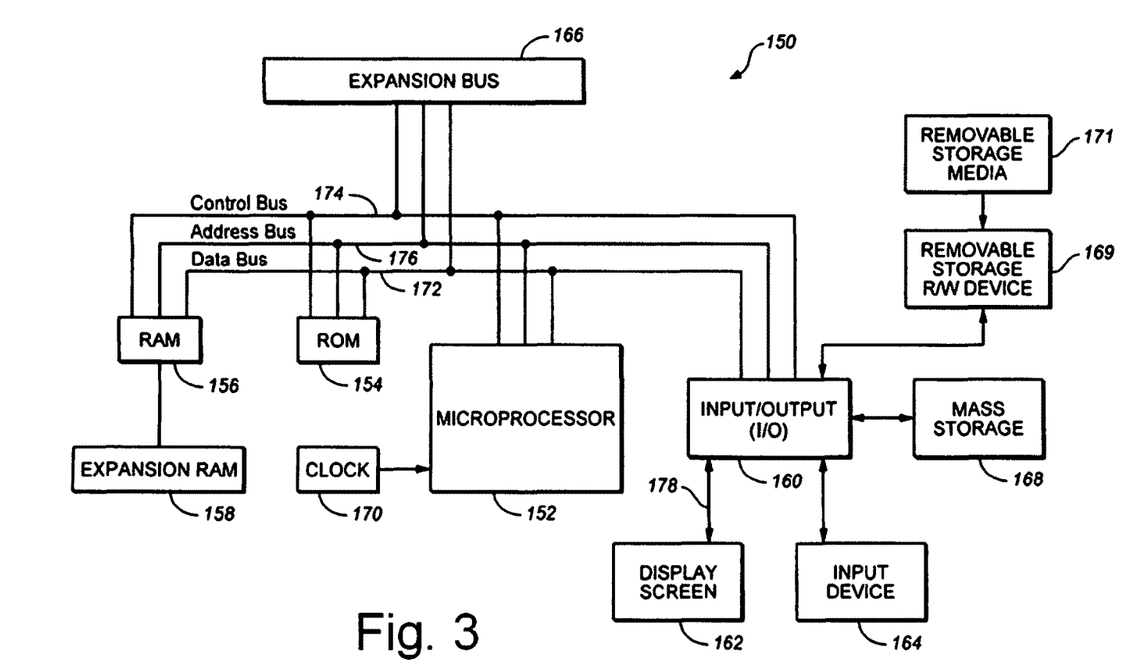
FIG. 3 is a block diagram of a general purpose computer system, representing one suitable computer platform for implementing the communication nodes illustrated in FIG. 2.

FIG. 3 illustrates a block diagram of a general purpose computer system which can be used to implement terminals 31 and 32. Specifically, FIG. 3 shows a general purpose computer system 150 for use in practicing the present invention. As shown in FIG. 3, computer system 150 includes a central processing unit (CPU) 152, read-only memory (ROM) 154, random access memory (RAM) 156, expansion RAM 158, input/output (I/O) circuitry 160, display assembly 162, input device 164, and expansion bus 166. Computer system 150 may also optionally include a mass storage unit 168 such as a disk drive unit or nonvolatile memory such as flash memory and a real-time clock 170.

CPU 152 is coupled to ROM 154 by a data bus 172, control bus 174, and address bus 176. ROM 154 contains the basic operating system for the computer system 150. CPU 152 is also connected to RAM 156 by busses 172, 174, and 176. Expansion RAM 158 is optionally coupled to RAM 156 for use by CPU 152. CPU 152 is also coupled to the I/O circuitry 160 by data bus 172, control bus 174, and address bus 176 to permit data transfers with peripheral devices.

I/O circuitry 160 typically includes a number of latches, registers and direct memory access (DMA) controllers. The purpose of I/O circuitry 160 is to provide an interface between CPU 152 and such peripheral devices as display assembly 162, input device 164, and mass storage 168.

Display assembly 162 of computer system 150 is an output device coupled to I/O circuitry 160 by a data bus 178. Display assembly 162 receives data from I/O circuitry 160 via bus 178 and displays that data on a suitable screen.

The screen for display assembly 162 can be a device that uses a cathode-ray tube (CRT), liquid crystal display (LCD), or the like, of the types commercially available from a variety of manufacturers. Input device 164 can be a keyboard, a mouse, a stylus working in cooperation with a position-sensing display, or the like. The aforementioned input devices are available from a variety of vendors and are well known in the art.

Some type of mass storage 168 generally is considered desirable. However, mass storage 168 can be eliminated by providing a sufficient mount of RAM 156 and expansion RAM 158 to store user application programs and data. In that case, RAMs 156 and 158 can optionally be provided with a backup battery to prevent the loss of data even when computer system 150 is turned off. However, it is generally desirable to have some type of long term mass storage 168 such as a commercially available hard disk drive, nonvolatile memory such as flash memory, battery backed RAM, PC-data cards, or the like.

A removable storage read/write device 169 may be coupled to I/O circuitry 160 to read from and to write to a removable storage media 171. Removable storage media 171 may represent, for example, a magnetic disk, a magnetic tape, an opto-magnetic disk, an optical disk, or the like.

In operation, information is input into the computer system 150 by typing on a keyboard, manipulating a mouse or trackball, or "writing" on a tablet or on a position-sensing screen of display assembly 162. Also, voice activation means can be utilized to input information into the computer system 150. CPU 152 then processes the data under control of an operating system and an application program, such as a program to perform steps of the inventive method described below, stored in ROM 154 and/or RAM 156. CPU 152 then typically produces data which is output to the display assembly 162 to produce appropriate images on its screen.

Expansion bus 166 is coupled to data bus 172, control bus 174, and address bus 176. Expansion bus 166 provides extra ports to couple devices such as network interface circuits, modems, display switches, microphones, speakers, etc. to CPU 152. Network communication is accomplished through the network interface circuit and an appropriate network.

Suitable computers for use in implementing the present invention may be obtained from various vendors. Various other types of computers, however, may be used depending upon the size and complexity of the required tasks. Suitable computers include mainframe computers, multiprocessor computers, workstations or personal computers.

In use, the computer-executable process steps according to the present invention typically initially are stored in mass storage 168, downloaded from mass storage 168 to RAM 156, and then executed by microprocessor 152 out of RAM 156. The process steps according to the present invention may also be stored on any form of computer-readable medium, including solid state memory devices such as RAM and ROM, optical storage devices such as CD-ROM and DVD, and magnetic storage devices such as hard disks, floppy disks, magnetic tapes and others.

Also connected to Internet backbone 50 is a hub 60. As discussed in more detail below, one function performed by the hub 60 is to retrieve messages sent over the Internet 50, process those instructions, and communicate with a central home controller. For this purpose, hub 60 also is connected to wide area network (WAN) 70.

Although terminals 31 and 32 are shown in FIG. 2 as being attached to hub 60 via the Internet 50, other methods can also be used for communicating between remote terminals and the hub, such as by utilizing a direct modem/telephone line dial-in connection, a wide area network, a local area network (LAN), or any other communication system. Furthermore, different terminals may be connected to hub 60 via different communication systems.

Preferably, the hub 60 will maintain a web site on the World Wide Web (WWW) serving as a host server, or may maintain a site that is connected through the Internet but not through the WWW. In this respect, the hub 60 functions as a web site host server.

It should be noted that a system implementing the present invention can be configured in many different ways and still be within the scope of the invention. The specific embodiments described herein are examples only. The benefit of maintaining a web site on hub 60 is that the system can be utilized by multiple consumers.

Although the present invention has been described in detail with regard to the exemplary embodiments and drawings thereof, it should be apparent to those skilled in the art that various adaptations and modifications of the present invention may be accomplished without departing from the spirit and the scope of the invention. Accordingly, the invention is not limited to the precise embodiments shown in the drawings and described in detail above. Therefore, it is intended that all such variations not departing from the spirit of the invention be considered as within the scope thereof.

The invention claimed is:

1. A method of modifying a music file to induce a desired state of consciousness, comprising the following steps:
   (a) Introducing a first brain entrainment modulation of a first target frequency into the music file;
   (b) introducing a second brain entrainment modulation of a second target frequency into said music file;
   (c) introducing a third brain entrainment modulation of a first auxiliary frequency into said music file;
   (d) introducing a fourth brain entrainment modulation of a second auxiliary frequency into said music file, wherein said second auxiliary frequency is generated by a first base window frequency and a second base window frequency and wherein the second auxiliary frequency divided by said first base window frequency is approximately the Golden Ratio;
   (e) and, introducing a fifth brain entrainment modulation of a binding frequency, wherein each of said first target, second target, first auxiliary, second auxiliary, and binding frequencies is different than the other frequencies and wherein, when the music file is played, said first, second, third, fourth, and fifth brain entrainment modulations are played simultaneously.

2. The method of claim 1 wherein said first target frequency is in the beta range, said second target frequency is in the beta range, said first auxiliary frequency is in the alpha range, said second auxiliary frequency is in the theta range and said binding frequency is in the gamma range.

3. The method of claim 1 wherein said first target frequency is in the delta range, said second target frequency is in the delta range, said first auxiliary frequency is in the alpha range, said second auxiliary frequency is in the fast range and said binding frequency is in the fast range.

4. The method of claim 1 wherein said first target frequency is in the theta range, said second target frequency is in the delta range, said first auxiliary frequency is in the alpha range, said second auxiliary frequency is in the fast range and said binding frequency is in the gamma range.

5. The method of claim 1 wherein said first target frequency is in the alpha range, said second target frequency is in the beta range, said first auxiliary frequency is in the alpha range, said second auxiliary frequency is in the fast range and said binding frequency is in the gamma range.

6. The method of claim 1 wherein said first target frequency is in the alpha range, said second target frequency is in the alpha range, said first auxiliary frequency is in the fast range, said second auxiliary frequency is in the fast range and said binding frequency is in the gamma range.

7. The method of claim 1 wherein said second base window frequency divided by said second auxiliary frequency is approximately the Golden Ratio.

8. A method of modifying a music file to induce a desired state of consciousness, comprising the following steps:
(a) Introducing a first brain entrainment modulation of a first target frequency into the music file;
(b) introducing a second brain entrainment modulation of a second target frequency into said music file;
(c) introducing a third brain entrainment modulation of a third target frequency into said music file;
(d) introducing a fourth brain entrainment modulation of a fourth target frequency into said music file;
(e) and, introducing a fifth brain entrainment modulation of an auxiliary frequency, wherein each of said first target, second target, third target, fourth target, and auxiliary frequencies is different than the other frequencies, wherein, when the music file is played, said first, second, third, fourth, and fifth modulations are played simultaneously, wherein said auxiliary frequency is generated using a first base window frequency and a second base window frequency, and wherein said auxiliary frequency divided by said first base window frequency is approximately the Golden Ratio.

9. The method of claim 8 wherein said first target frequency is in the delta range, said second target frequency is in the delta range, said third target is in the alpha range, said fourth target frequency is in the fast range and said auxiliary frequency is in the fast range.

10. The method of claim 8 wherein said first target frequency is in the theta range, said second target frequency is in the delta range, said third target is in the alpha range, said fourth target frequency is in the fast range and said auxiliary frequency is in the fast range.

11. The method of claim 8 wherein the additional following step is performed:
(f) introducing a sixth brain entrainment modulation of a binding frequency into said music file.

12. The method of claim 11 wherein said binding frequency is in the gamma range.

13. The method of claim 8 wherein said second base window frequency divided by said auxiliary frequency is approximately the Golden Ratio.

14. A method of modifying a music file to induce a desired state of consciousness, comprising the following steps:
(a) Introducing a first brain entrainment modulation of a first target frequency into the music file;
(b) introducing a second brain entrainment modulation of a second target frequency into said music file;
(c) introducing a third brain entrainment modulation of a third target frequency into said music file;
(d) and, introducing a fourth brain entrainment modulation of an auxiliary frequency, wherein each of said first target, second target, third target, and auxiliary frequencies is different than the other frequencies and wherein, when the music file is played, said first target, second target, third target, and auxiliary brain entrainment modulations are played simultaneously, wherein said auxiliary frequency is generated using a first base window frequency and a second base window frequency, and wherein said auxiliary frequency divided by said first base window frequency is approximately the Golden Ratio.

15. The method of claim 14 wherein said first target frequency is in the theta range, said second target frequency is in the alpha range, said third target is in the fast range, and said auxiliary frequency is in the fast range.

16. The method of claim 14 wherein said second base window frequency divided by said auxiliary frequency is approximately the Golden Ratio.

* * * * *